United States Patent [19]

Hussami

[11] Patent Number: 5,382,884
[45] Date of Patent: Jan. 17, 1995

[54] MEANS AND METHOD FOR TESTING VOLATILE MATERIAL

[75] Inventor: Imran S. Hussami, Wichita, Kans.

[73] Assignee: Texaco Inc., White Plains, N.Y.

[21] Appl. No.: 875,949

[22] Filed: Apr. 30, 1992

[51] Int. Cl.$^6$ .................. G05B 19/04; F27B 14/10; G01N 25/00
[52] U.S. Cl. .................. 318/567; 73/863.11; 414/172; 422/67; 432/156
[58] Field of Search ................ 73/863, 863.01, 863.11, 73/864.81; 141/83; 177/50; 414/21, 147, 172, 186, 222; 422/63, 67, 68.1, 78, 99; 432/120, 121, 122, 156; 436/43, 147, 155, 157, 174, 177, 908; 318/256, 280, 567, 430, 431

[56] References Cited

U.S. PATENT DOCUMENTS 3,620,288 11/1971 Barrow .
4,158,536 6/1979 Willay et al. .
4,391,774 7/1983 Dupain .
4,693,867 9/1987 Commarmot et al. .
4,952,108 8/1990 Weigand et al. .

Primary Examiner—Bentsu Ro
Attorney, Agent, or Firm—Kenneth R. Priem; Ronald G. Gillespie; Harold J. Delhommer

[57] ABSTRACT

The present invention includes a crucible which holds volatile material to be tested. The crucible is lowered into an oven apparatus and removed from the oven apparatus by equipment programmed in a predetermined manner.

3 Claims, 5 Drawing Sheets

MEANS AND METHOD FOR TESTING VOLATILE MATERIAL

BACKGROUND OF THE INVENTION

Field of the Invention

The present invention relates to laboratory testing means and methods in general and, more particularly, to laboratory testing means and methods for testing volatile material.

SUMMARY OF THE INVENTION

The present invention includes a crucible which holds volatile material to be tested. The crucible is lowered into an oven apparatus and removed from the oven apparatus by equipment programmed in a predetermined manner.

The objects and advantages of the present invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
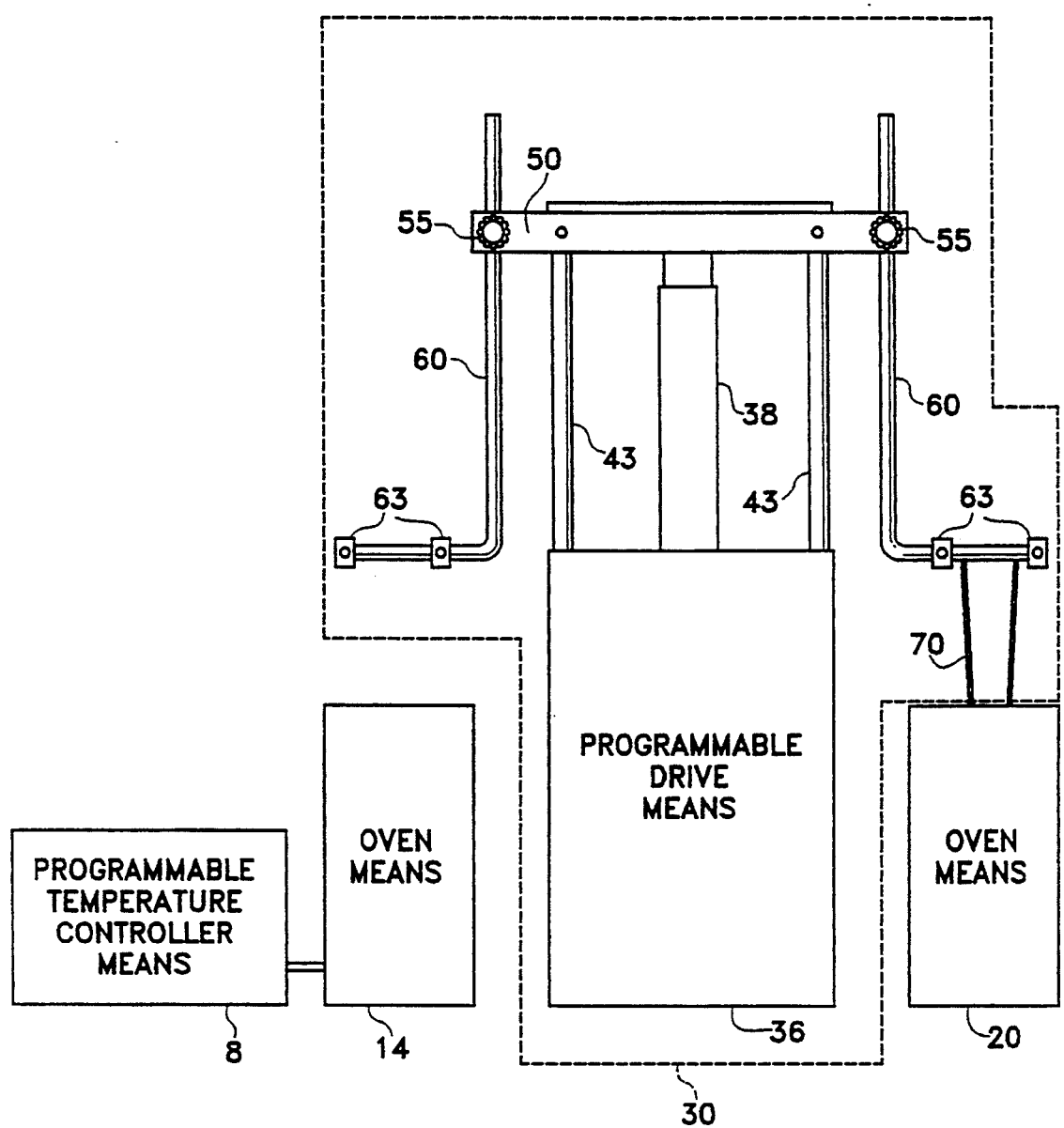
FIG. 1 is a partial simplified block diagram and partial schematic drawing of apparatus, constructed in accordance with the present invention for the testing of volatile material.

Referring now to FIG. 1 there is shown an arrangement of apparatus for testing volatile matter. The apparatus includes a programmable temperature controller means 8 which is electrically connected to oven means 14 and 20. Temperature controller means 8 may be of the 900 series type provided by the Love Controls Corporation. It should be noted that the electrical connection between programmable temperature controller means 8 and oven means 20 is not shown so as to avoid confusion. That electrical connection will be shown later in FIG. 4.

Associated with oven means 14 and 20, and having a spatial relationship therewith, is vertical moving means 30. Vertical moving means 30 include programmable drive means 36, which will be discussed in more detail hereinafter, having a drive element 38 associated with guide rods 43. Affixed to drive element 38 is an arm element 50 which has a hole in each end cooperating an adjustment knob 55. A holder arm 60 passes through each hole in arm 50 and is maintained in place by knob 55. Thus, arm 60 can be raised or lowered to a desired position through adjustment of knob 55. Also, arm 60 has stops 63 which allows it to position a crucible holder 70 in the horizontal plane.

Figure 2:
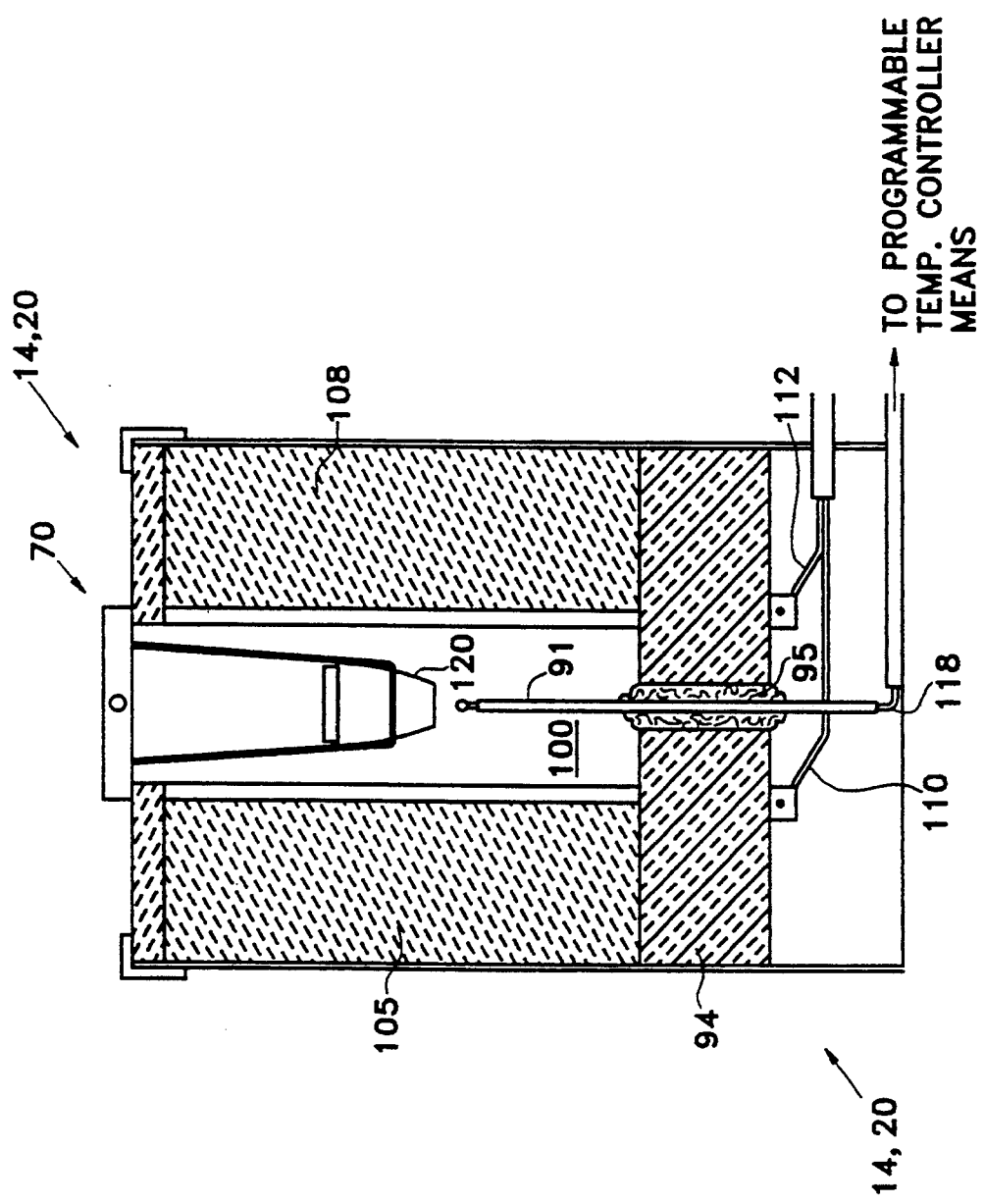
FIG. 2 is a graphical representation of the crucible and the crucible holder shown in FIG. 1.

Referring now to FIG. 2, there is shown oven means 14 or 20 which includes an oven of the type part number FA-120 manufactured by Hoskin Manufacturing. Each oven means 14 or 20, as shown in FIG. 2, has a thermistor 91 inserted through a bottom of insulating material 94 and sealed in place by insulating wool 95. Located in insulated material 94 is a heating element, which is not shown, but suffice to say that the heating element although it appears to be located within insulating material 94 actually has exposure to a chamber 100 formed by insulating sides 105 and 108. The heating element heats chamber 100. The heating element is connected to the programmable temperature controller means 8 by electrical wires 110 and 112. Thermistor 91 is also connected to programmable temperature controller means 8 by wires 118. Oven means 14 or 20 has an opening to chamber 100 through which crucible holder 70 may enter and leave chamber 100. Also shown in FIG. 2 is crucible holder 70 holding crucible 120.

Figure 3:
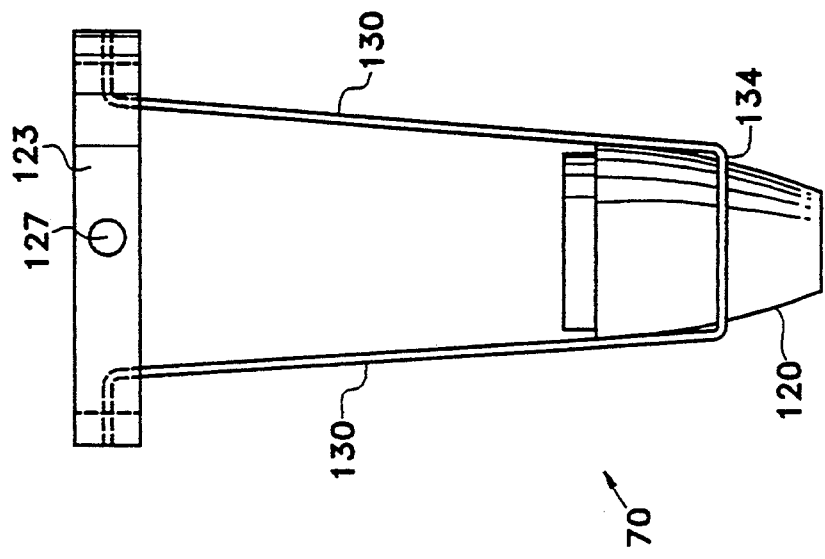
FIG. 3 is a graphical representation of the oven means shown in FIG. 1.

Referring now to FIG. 3, crucible holder 70 is shown in more detail holding crucible 120. Holder 70 has a collar 123 having a hole 127 drilled forth for the passage of arm 60. Holder 70 has wire supports 130 affixed to a circular wire bottom piece 134.

Figure 4:
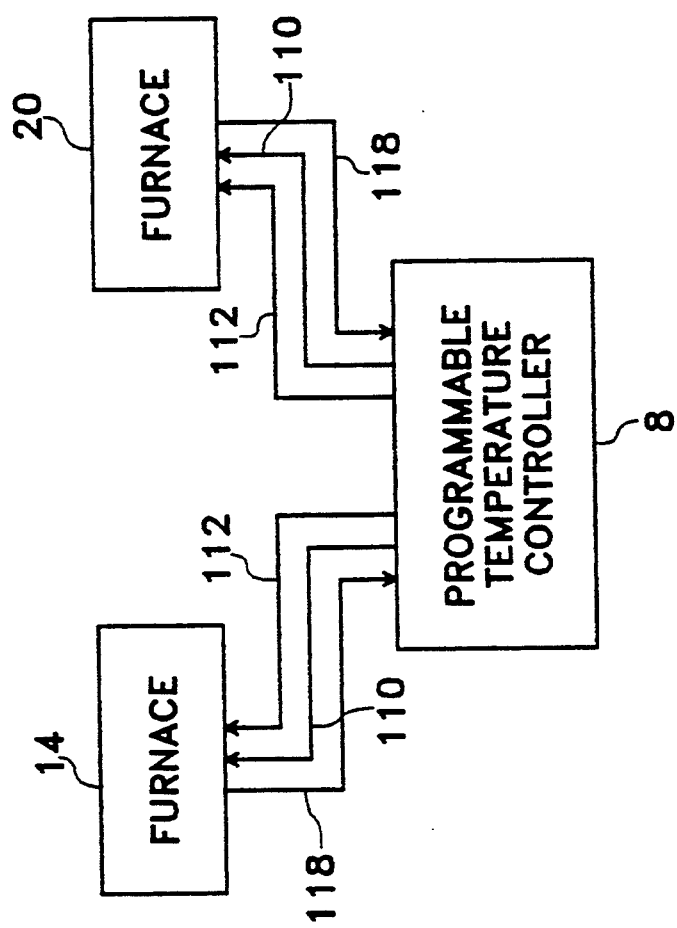
FIG. 4 is a simplified block diagram of the temperature controlling apparatus shown in FIG. 1.

Referring now to FIG. 4, temperature controller means 8 maintains the temperature of oven means 14 and 20 at a predetermined temperature. It should be noted that the unit may control the temperatures of furnaces 14 and 20 independently of each other so that they can be kept at different temperatures.

Figure 5:
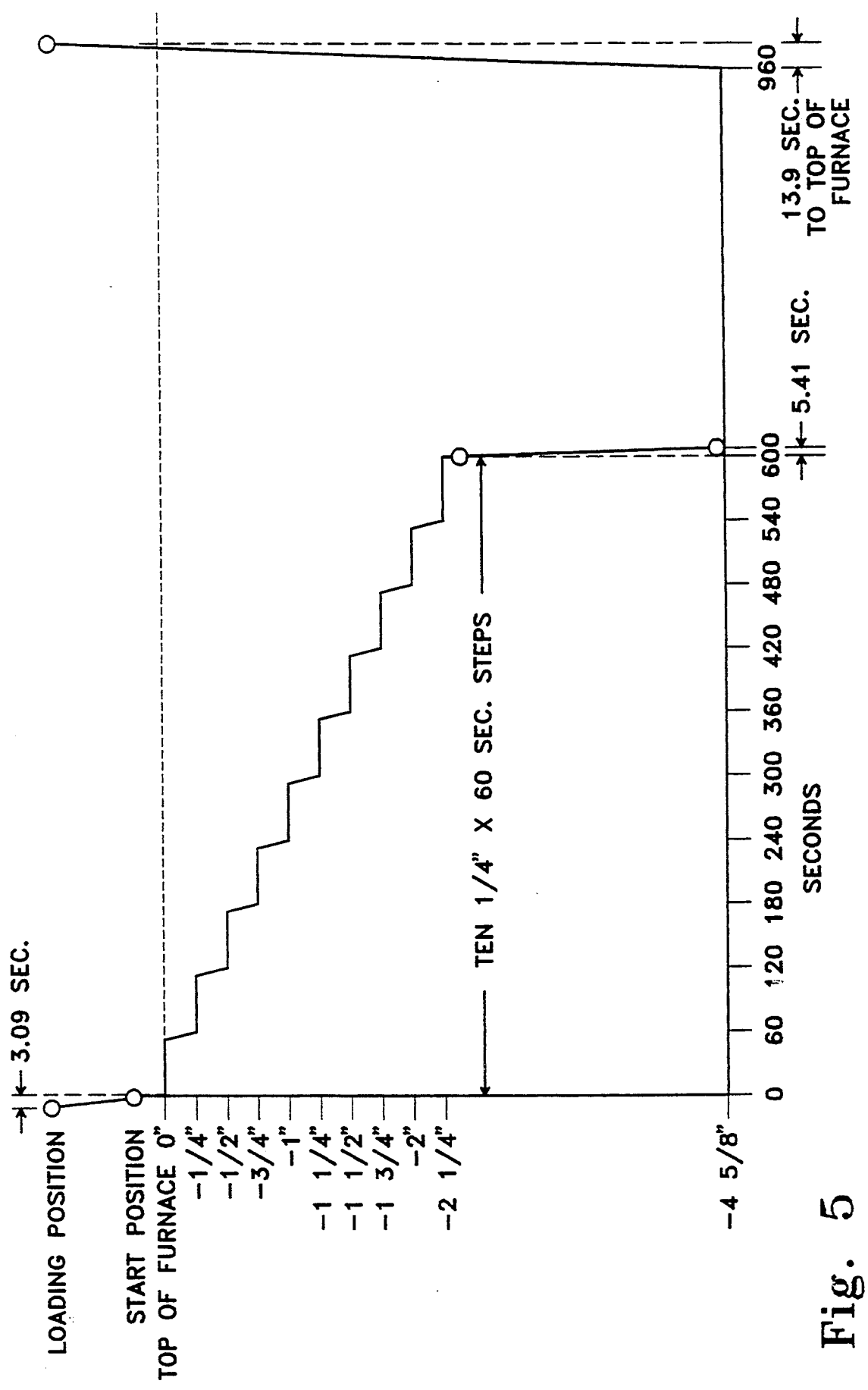
FIG. 5 is a plot relating distances associated with the oven means to time.
Figure 6:
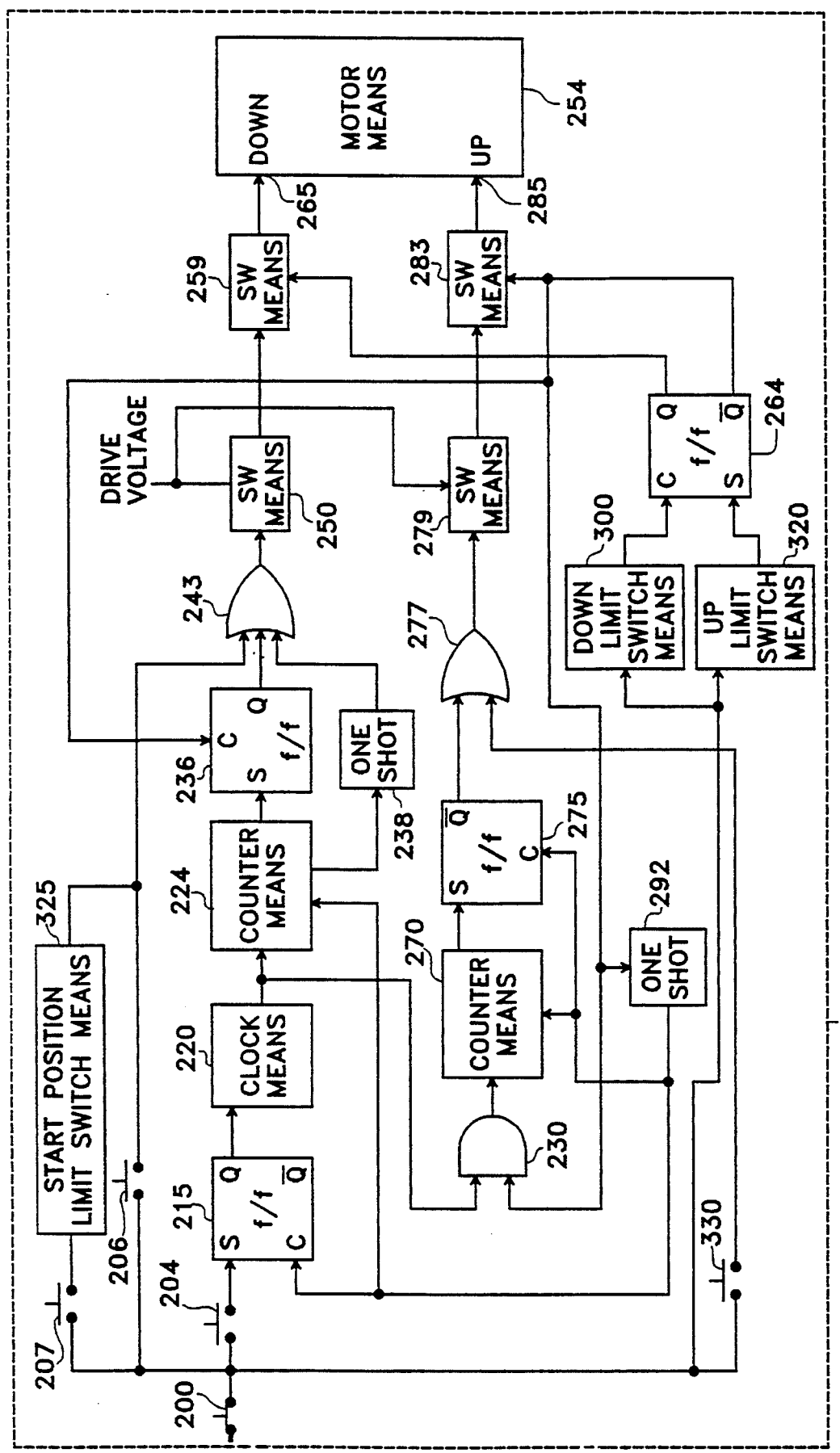
FIG. 6 is a detailed block diagram of the programmable drive means shown in FIG. 1.

With reference now to FIG. 5 and 6, FIG. 5 shows a typical crucible heating operation relating time to distance for utilizing the present invention. There is a loading position in which a crucible 120 is filled with volatile material and is then lowered as hereinafter explained, to a start position. The start position is a point just above the top of oven means 14 or 20 which is at time zero at the start of a test. An operator initiates a test by pressing a start button. Crucible 120 is lowered to the top of the oven means 14 or 20 and stay there for approximately sixty seconds. Crucible 120 is then lowered in steps of a quarter of an inch per sixty seconds until finally the crucible is at a depth of $2\frac{1}{4}$ inches into chamber 100 of oven means 14 or 20. At which time programmable drive means 36 lowers crucible 120 down $4\frac{5}{8}$ inches more into oven means 14 or 20 where it is kept for approximately 360 seconds or 6 minutes. At the end of this time interval programmable drive means 36 returns crucible 120 back to the loading position.

With reference to FIG. 6, programmable drive means 36 includes a push button switch 200 which is used for stopping the operation of programmable drive means. Switch 200 is in a normally closed position until activated. A voltage is applied to switch 200, passes through and is provided to a momentary type push button switch 204 which is the start button for starting a test, and to momentary push button switches 206 and 207. Switch 204 is connected to the set input of a flip-flop 215 whose Q output is applied to the input of clock means 220. Clock means 220, when activated provides timing pulses to counter means 224 and to an AND gate 230.

The output of counter means 224 is applied to a one-shot multivibrator 236 and to the set input of a flip-flop 238. The Q output of flip-flop 236 and the output from one-shot 238 are provided to an OR gate 243 which is also connected to switch 206. The output from OR gate 243 is provided to switch means 250 receiving a drive voltage of sufficient power to drive a motor means 254 as hereinafter explained.

When the signal from OR gate 243 is at a high logic level, switch means 250 will pass the drive voltage to a another switch means 259 which is controlled by the Q output of a flip-flop 264 as hereinafter explained. When switch means 259 is rendered conductive, it provides the drive voltage to the down input 265 of motor means 254. When a drive voltage is applied to down input 265 of motor means 254, it will cause the motor means 264, which is mechanically linked to moveable drive member 38, to move drive member 38 in a down direction and hence will cause crucibles 120 and crucible holders 70 to also move in a down direction.

AND gate 230 receives the $\overline{Q}$ output from a flip-flop 264 and when enabled provides the timing pulses from clock means 220 to counting means 270. Counting means 270 provides an output at the end of a predetermined count, in this case corresponding to approximately six minutes, which triggers flip-flop 275 to a set state. The $\overline{Q}$ output of flip-flip 275 is provided through an OR gate 277, to switch means 279, which also receives the drive voltage. Switch means 279 passes the drive voltage to switch means 283 when the $\overline{Q}$ output of flip-flop 275 is at a high logic level.

Switch means 283, like its counterpart switch means 259, is similarly controlled by the $\overline{Q}$ output of flip-flop 264. The $\overline{Q}$ output of flip-flop 264 also triggers a one-shot multivibrator 292 which provides a pulse to the clear inputs of flip-flops 215, 275 and to the clear inputs of counting means 270, 224. The $\overline{Q}$ output of flip-flop 264 also enables AND gate 230 when it is at high logic level and disables AND gate 230 when it is at a low logic level.

Flip-flop 264 has its clear input connected to a "down" limit switch means 300 and a set input to an "up" limit switch means 320.

Momentary push button switch 206 is the "manual down" switch which allows an operator to override the program to lower a crucible 120 to its lowest point allowed by down limit switch means 300. Switch 206 is connected to OR gate 243.

Momentary push button switch 207 is connected to a "start position" limit switch means 325 which in turn is connected to OR gate 243. Switch means 207 is activated by the operator. As holder 70 and crucible 120 moves downward to a predetermined point "start position" limit switch means 325 is rendered non-conductive thereby stopping crucible holder 107 and crucible 120 at the start position as holder 70 and crucible 120 moves upward past the predetermined "start position" after the test is complete, switch means 325 is rendered conductive.

Switch means 300 and 320 are connected to switch 200. Another momentary push button switch 330 connects switch 200 to OR gate 277. Switch 330 allows the operator to manually raise holder 70 until the up limit switch means 320 is triggered.

In operation, with reference to FIGS. 1, 5 and 6, a crucible 120 containing volatile matter has been placed in crucible holder 70 which is attached to arm 60. The operator presses push button switch 207 until start position limit switch means 325 stops crucible 120 at the start position. The operator then presses push button switch 204, which momentarily closes it, thereby providing a trigger signal to the set input of flip-flop 215 causing flip-flop 215 to go to the set state. While in the set state, all flip-flops provide a high logic level Q output and a low logic level $\overline{Q}$ output. While in the clear state, the flip-flops provide a low logic level Q output and a high logic level $\overline{Q}$ output.

In effect, flip-flop 215 high logic level Q output enables clock means 220 to provide a series of clock pulses to counter means 224 and to AND gate 230. Counter means 224 counts the pulses and every time the pulses counted add up to 60 seconds, counter means 224 provides a trigger output to one-shot multivibrator 238. When one-shot 38 is triggered, it provides a pulse of a predetermined width through OR gate 243 to enable switch means 250 for duration of the pulse from one-shot 238. Enabled switch means 250 provides the drive voltage to switch means 257.

At this time flip-flop 264, as will hereinafter be explained, is in a set state and its Q output is at a high logic level thereby enabling switch means 259. Enabled switch means 259 passes the drive voltage to down input 265 of motor means 254. Motor means 254 is mechanically connected to the drive member 38 and causes drive member 38 to go down as long as the drive voltage is applied to down input 265. Thus, the drive voltage is applied to input 265 during the duration of the pulse from one shot 238 and hence is related to the predetermined time, in this case approximately 0.4 seconds. Obviously, once the pulse from multivibrator 238 ceases to exist, motor means 254 stops.

As the drive member 38 moves in a downward direction, crucible 70 is being lowered into chamber 100 of oven means 14 or 20. Thus, we can see that what has been described and what will take place for the next ten minutes is a lowering of crucible 120 into chamber 100 of oven 14 or 20 in a series of steps, approximately a quarter of an inch at a time. This allows a gradual heating of the volatile material allowing gases from the heated volatile material to escape. After ten minutes as shown in FIG. 5, counter means 24 provides another pulse to flip-flop 236 causing it to go to a set state. The high logic level Q output from flip-flop 236 passes through OR gate 243 to enable switch means 250.

Even though counter means 224 continues to provide pulses to one-shot 238, the pulses from one-shot 238 are now meaningless due to the effect of OR gate 243. Switch 250 is being controlled by the high logic level Q output from flip-flop 236. Motor means 254 drives down member 38 in a downward direction until down limit switch 300 is contacted and activated. When activated down limit switch means 300 triggers flip-flop 264 to a clear state. At this time, crucible 120, with the volatile matter, is essentially at its lowest desired point. While flip-flop 264 is in the clear state, the Q output goes to a low logic level thereby disabling switch means 259.

Further, the $\overline{Q}$ output of flip-flop 264 goes to a high logic level thereby enabling switch means 283 and AND gate 230. AND gate 230 is still receiving the timing pulses from clock means 220 and provides them to counter means 270. Counter means 270 starts to count and when it arrives at six minutes it provides a pulse output to flip-flop 275 causing its Q output to go to a high logic level thereby enabling switch means 279 to pass the drive voltage to switch means 279. Switch means 279 then provides the drive voltage to switch means 283 which, as noted earlier, has been rendered conductive by the $\overline{Q}$ output of flip-flop 264 so that it provides the drive voltage to an up input 285 of motor means 254. Motor means 254 will then move drive member 38 in an upward direction thereby causing the crucible 120 to be removed from the oven means, and continues in the upward direction until up limit switch means 320 is triggered which in turn triggers a flip-flop 264 to the set state.

The $\overline{Q}$ output of flip-flop 264 goes to a low logic level as a result of the triggering to the set state. The $\overline{Q}$ of flip-flop 264 in turns triggers a one-shot multivibrator 292 which provides a reset or clear pulse to flip-flops 215, 275 and to counter means 224 and 270. Further, the low logic level $\overline{Q}$ output from flip-flop 264 disables AND gate 230. The apparatus is now ready to start another test as soon as the operator refills crucible 120.

What is claimed is:

1. An apparatus for testing volatile material comprising:
   (a) a crucible for holding volatile material;
   (b) a crucible holder means for holding the crucible;
   (c) an oven having an open chamber for heating the volatile material;
   (d) a means for controlling the temperature of the oven;
   (e) a moving means for causing the crucible to enter the oven and withdraw from the oven in a predetermined manner,
   said moving means comprising:
      a reversible drive motor having an up input and a down input;
      a drive member cooperating with the drive motor to be driven either in an upward direction or a downward direction by the drive motor; and
      a header means affixed to the drive member and to the crucible holder means in a manner so that as the drive motor drives the drive member in an upward or downward direction, the drive member causes the crucible to move into and out of the oven chamber; and
   (f) a programmable means for controlling the drive motor so as to control the movement of the crucible,
   said programmable means comprising:
      a start means for providing clock pulses;
      a first switch means receiving a drive voltage for blocking or passing the drive voltage in accordance with a first control signal;
      means connected to the start means and to the first switch means for utilizing the clock pulses to provide a series of pulses to the first switch means as the first control signal; and
      a down limit means connected to the first switch means and to the down input of the drive motor for allowing the drive voltage from the first switch means to be applied to the down input of the drive motor and preventing the drive voltage from being applied to the drive motor's down input when the crucible is at a lowest desired position within the oven.

2. Apparatus as claimed in claim 1 in which the programmable means further comprises:
   second switch means receiving the drive voltage for blocking or passing the drive voltage in accordance with a second control signal, and
   means connected to the start means and to the down limit means for providing the second control signal to the second switch means after a predetermined time interval has elapsed since the crucible has reached the lowest desired position, and
   up limit means connected to the second switch means and to the up input of the drive motor for allowing the drive voltage from the second switch means to be applied to the up input of the drive motor and preventing the drive voltage from being applied to the drive motor's up input when the crucible is at a highest desired position outside of the oven.

3. Apparatus as defined in claim 2 further comprising means for overriding the programmable means so as to cause the crucible to move in a downward direction until it reaches the lowest desired position, and
   means for overriding the programmable means for causing the crucible to move in an-upward direction until it reaches the highest desired position.

* * * * *